United States Patent [19]

Hughes et al.

[11] Patent Number: 4,640,617

[45] Date of Patent: Feb. 3, 1987

[54] SPECTROMETERS HAVING PURGE RETENTION DURING SAMPLE LOADING

[75] Inventors: Norman S. Hughes, San Clemente; Walter M. Doyle, Laguna Beach, both of Calif.

[73] Assignee: Laser Precision Corporation, Utica, N.Y.

[21] Appl. No.: 707,022

[22] Filed: Feb. 28, 1985

[51] Int. Cl.[4] .............................................. G01N 21/13
[52] U.S. Cl. .................. 356/326; 250/441.1; 356/346; 356/244
[58] Field of Search ............... 356/326, 328, 319–325, 356/244, 246, 346; 250/441.1

[56] References Cited

U.S. PATENT DOCUMENTS 2,602,899  7/1952  Page .................................. 250/441.1
3,580,685  5/1971  Eriksson ............................. 356/244

*Primary Examiner*—F. L. Evans
*Attorney, Agent, or Firm*—Thomas J. Plante

[57] ABSTRACT

Spectrometer sampling chamber structures are disclosed which avoid purge loss during loading and unloading of samples. In two disclosed versions, a plunger carries the sample, and fits closely inside a fixed tube, into which it is inserted for sample illumination. Sample loading and unloading is accomplished without fully removing the plunger from the tube. Also, an automatic purging flow of gas from the interior of the spectrometer is caused during insertion of a new sample. In a third disclosed version, vertically stacked sample holders move through a vertical chute into which they are inserted to the top of the sample chamber, and from which they are removed at the bottom of the sample chamber.

20 Claims, 21 Drawing Figures

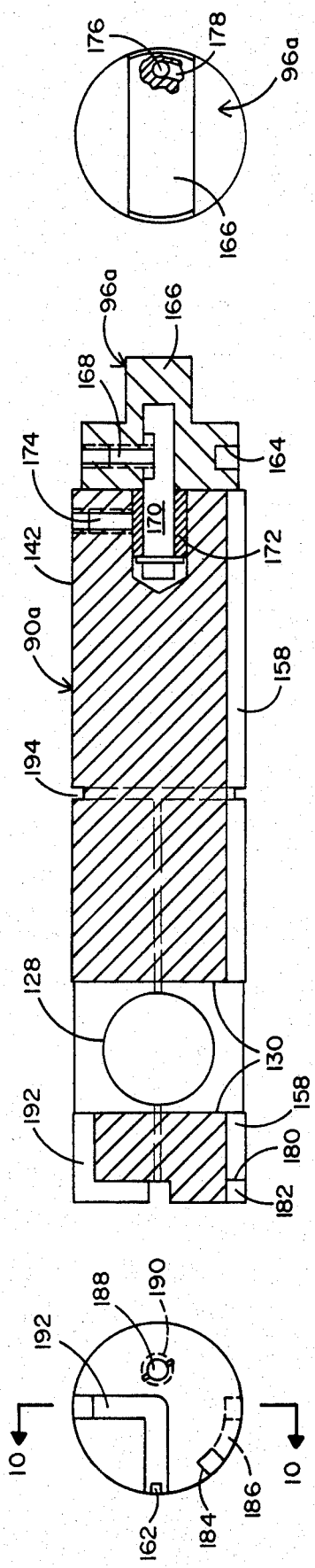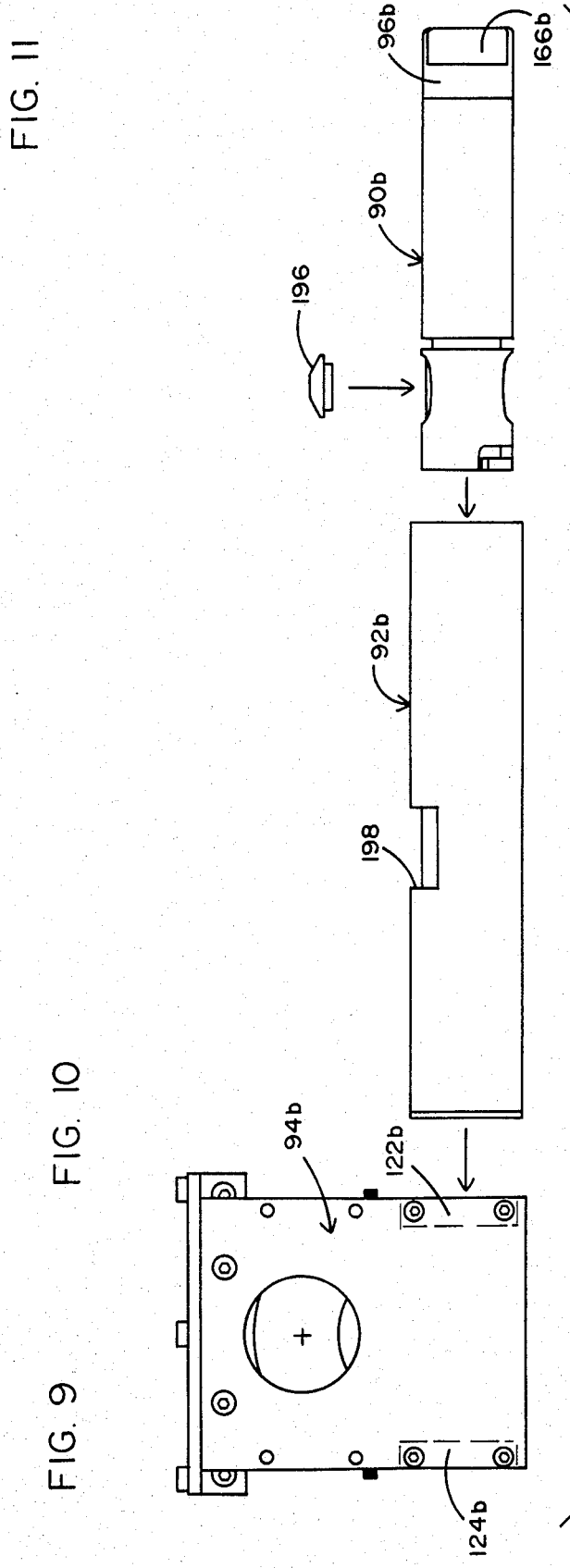

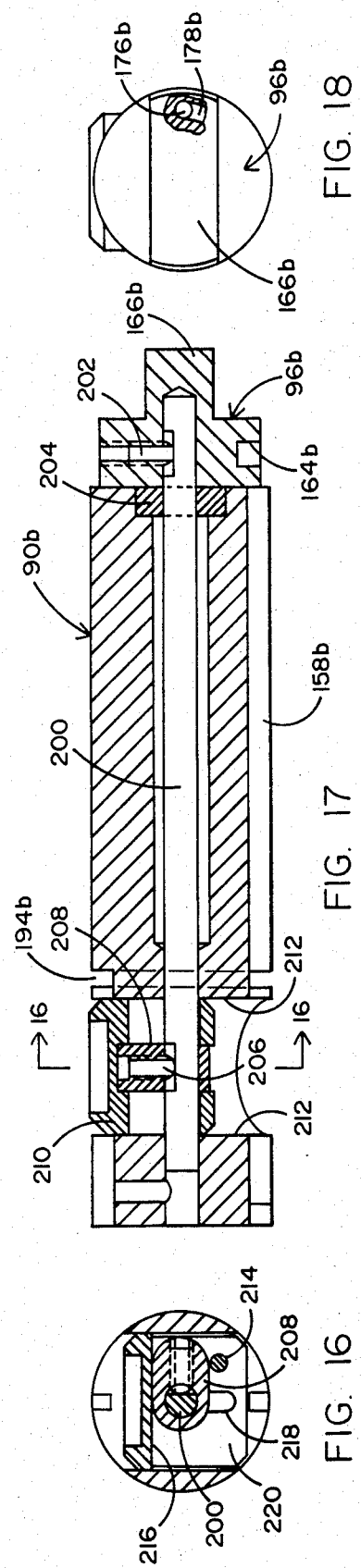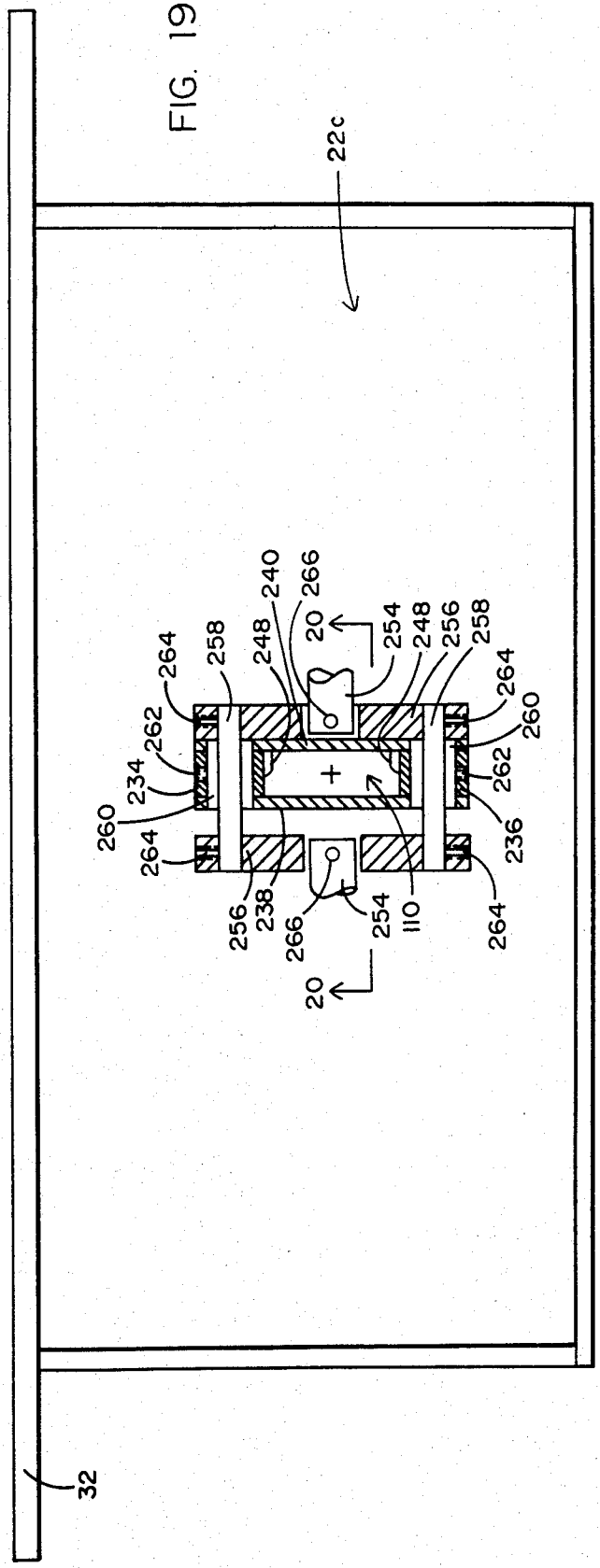

SPECTROMETERS HAVING PURGE RETENTION DURING SAMPLE LOADING

BACKGROUND OF THE INVENTION

This invention relates to spectrometer systems, and particularly to sample loading and unloading devices, and methods, which avoid purge loss during sample interchange in the sample chambers of spectrometers.

Saving time in spectrometry operations can be accomplished by improving various segments of the overall analytical process. A significant, but neglected, approach to time saving is elimination of the time required for "purging" the system. In order to avoid artifacts in the analytical data, it is customary to conduct the analytical process in an enclosed chamber, from which both water vapor and carbon dioxide are eliminated. This is usually accomplished by injecting dry nitrogen gas continuously into the chamber, in such a way that it "flushes out" the normal atmosphere, which would otherwise be present, and keeps the chamber filled with nitrogen.

The assignee of this application has developed a spectrometer system which operates in conjunction with any of a variety of modular sampling chambers. The entire system is designed to operate more efficiently, primarily by eliminating waste of time throughout the analytical process. Time saving is important in any situation, but it is particularly important where the instrument is being used for quality control during manufacturing processes.

The use of modular sampling chambers, which are "hung on" the main body of the spectrometer, facilitates access to the sample. The present invention employs that ease of access to eliminate the need for purging between samples. While the same concepts might be adapted to sample loading in other spectrometer configurations, they are particularly useful in conjunction with the modular sampling chambers.

SUMMARY OF THE INVENTION

The present invention provides a sample insertion structure which permits sample loading and unloading with minimal atmosphere leakage into the enclosed area, and in certain instances with an automatic purging of the space around the incoming sample during its movement into the sample-illuminating position.

In each embodiment, the sample is mounted in a supporting structure which is closely fitted inside a round, or rectangular, guiding channel extending into the sample chamber. The mechanism is such that the sample after insertion is securely retained in the proper position during sample illumination.

In certain embodiments, the sample supporting structures are retracted for sample interchange; and in at least one embodiment the sample supporting structures enter through the top of the sample chamber and exit through the bottom of the sample chamber.

BRIEF DESCRIPTION OF THE DRAWINGS

FIG. 6-11 show in detail the zero purge loss apparatus of FIG. 3, in which sample-illumination involves light transmittance through the sample; FIG. 6 is an exploded view of the components of the apparatus; FIGS. 7 and 8 are, respectively, a longitudinal cross-section, and an end view, of the outer guiding tube; and FIGS. 9, 10 and 11 are, respectively, a left end view, a longitudinal cross-section, and a right end view, of the sample-carrying plunger which fits into the guiding tube;

FIGS. 12–18 show in detail the zero purge loss apparatus of FIG. 4, in which the sample-illumination involves light reflectance from the sample; FIG. 12 is an exploded view of the components of the apparatus; FIG. 13 is a front elevation of the unit mounted in the sampling module which carries the paraboloid reflectance mirrors, and also the outer guiding tube of the sample insertion apparatus; FIGS. 14 and 15 are, respectively, a longitudinal cross-section, and an end view, of the outer guiding tube; and FIGS. 16, 17 and 18 are, respectively, a left end view, a longitudinal cross-section, and a right end view, of the sample-carrying plunger which fits into the guiding tube; and FIGS. 19–21 show in detail the zero purge loss apparatus of FIG. 5, in which samples are inserted through the top, and removed through the bottom, of the modular sampling chamber; FIG. 19 is a partly sectional top view of the sampling chamber; FIG. 20 is a partly sectional front elevation of the sampling chamber; and FIG. 21 is a side elevation of the sampling chamber.

DETAILED DESCRIPTION OF SPECIFIC EMBODIMENTS

Figure 1:
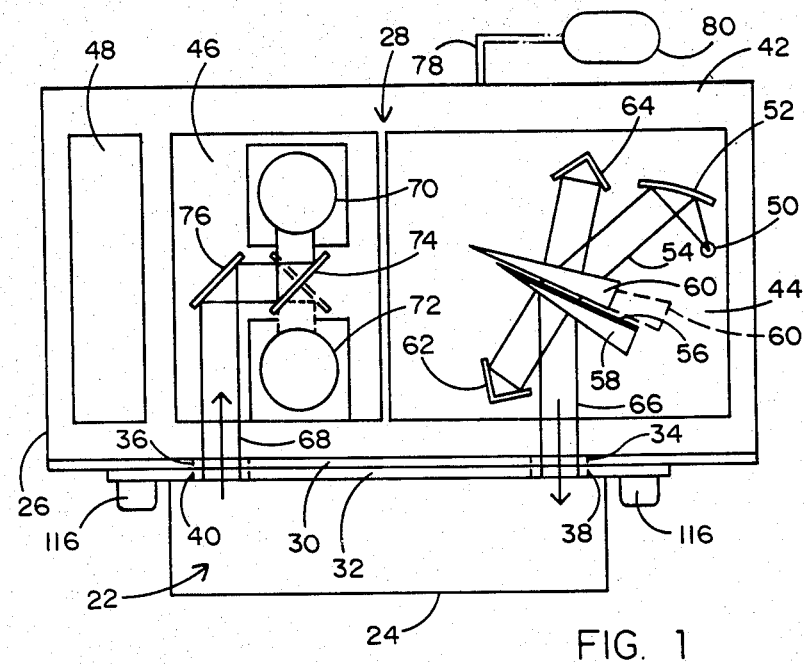
FIGS. 1 and 2 show a spectrometer having a modular sampling chamber.
Figure 2:
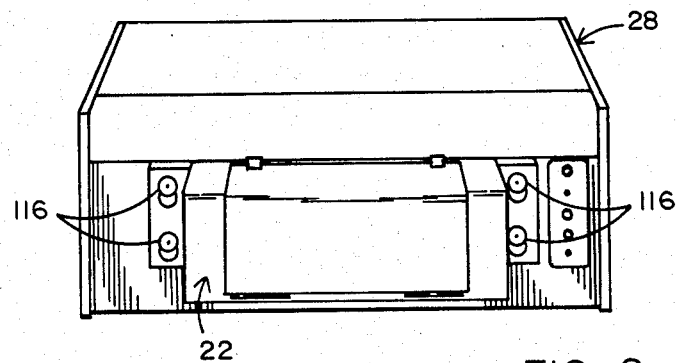

As shown in FIGS. 1 and 2, an interchangeable sampling module 22 includes pre-arranged and pre-aligned sample-illuminating optics located inside a housing 24, which is separate from, but readily attachable to, and detachable from, a housing 26 containing an interferometer/detector module 28. Both housings 24 and 26 are enclosed during spectrometer operation, except for aligned apertures, through which pass two laterally-spaced collimated radiation beams. One pair of aligned apertures transmits a collimated beam from the interferometer to the sample module, and another pair of aligned apertures transmits a collimated beam from the sample module to the detector.

As seen in FIG. 1, the side of the interferometer/detector module 28 which is engaged by the sampling module 22 has an interface panel 30, to which is clamped the rear wall 32 of whichever sampling module is currently in use. Interface panel 30 has two spaced apertures 34 and 36, which are aligned, respectively, with spaced apertures 38 and 40 in wall 32.

Inside the housing 26 of the interferometer/detector module, separate sub-assemblies may be mounted on supporting plates, which are secured to the floor 42 of housing 26. For example, the interferometer portion may be carried on a plate 44, the detector portion may be carried on a plate 46, and the electronics portion may be carried on a plate 48.

The interferometer in FIG. 1 includes a radiation source 50 and optics 52 which direct a collimated beam 54 toward a beamsplitter coating 56 located on the inner surface of a non-moving wedge-shaped prism 58. A moving wedge-shaped prism 60, which has the same dimensions as prism 58, causes spectral scanning of the interferometer. The beam-splitter 56 transmits part of the source radiation along one interferometer arm toward a first stationary corner reflector 62, and reflects part of the source radiation along the other interferometer arm toward a second stationary corner reflector 64. The returning collimated beams from the respective reflectors 62 and 64 are recombined at beamsplitter 56; and a recombined collimated beam 66 exits the interferometer and enters the sampling module through aligned apertures 34 and 38.

After sample illumination in the sampling module, a collimated beam 68 exits the sampling module and enters the detector portion of the system through aligned apertures 40 and 36. The detectors convert the optical signals into electronic signals for suitable electronic processing. In FIG. 1, two detectors 70 and 72 are shown, which may provide alternative types of detection. Selection of the detector is controlled by moving a "detector-switching" flat mirror 74 either to a position in which radiation is directed to detector 72 or to a position in which radiation is directed to detector 74. Another flat mirror 76 may be needed to direct beam 68 toward mirror 74. One detector may be a general purpose, broad band detector, and the other may be a mercury-cadmium-telluride cooled detector optimized for high sensitivity.

The collimated beams 66 and 68 which enter and leave the sampling module 22 are preferably, although not necessarily, parallel to one another. Parallelism of the beams tend to simplify the optical arrangements within the various interchangeable sampling modules.

The present application is primarily concerned with the problem of "purge" retention in the spectrometer system, because of the significant time saving possible if purge loss is avoided during loading and unloading of samples.

Purge retention is a significant problem in spectrometer systems because most spectrometer analyses should be performed in a special gas environment, such as dry nitrogen. If the experiments were performed in normal atmospheric conditions, undesired optical artifacts would be introduced, primarily by water vapor and by carbon dioxide.

In order to avoid these sources of inaccuracy the entire spectrometer should be enclosed, and maintained in a "purged" atmosphere. The purging is accomplished by admitting dry nitrogen at one point, and permitting the normal atmosphere to escape at any closed but unsealed locations. Normally purging is accomplished by connecting a hose 78 (see FIG. 1) from the rear of the main body to a source of nitrogen, which may be a suitably valved tank 80 containing liquid nitrogen. The purging gas is retained in communication with the spectrometer throughout the series of analytical procedures. After initial purging has been completed, the experiments may be started. Since initial purging is a time-consuming process, it is highly desirable to avoid intrusion of atmosphere, i.e., loss of purge, during the interchanging of samples. The present invention permits the attainment of substantially zero purge loss during sample interchange.

Figure 3:
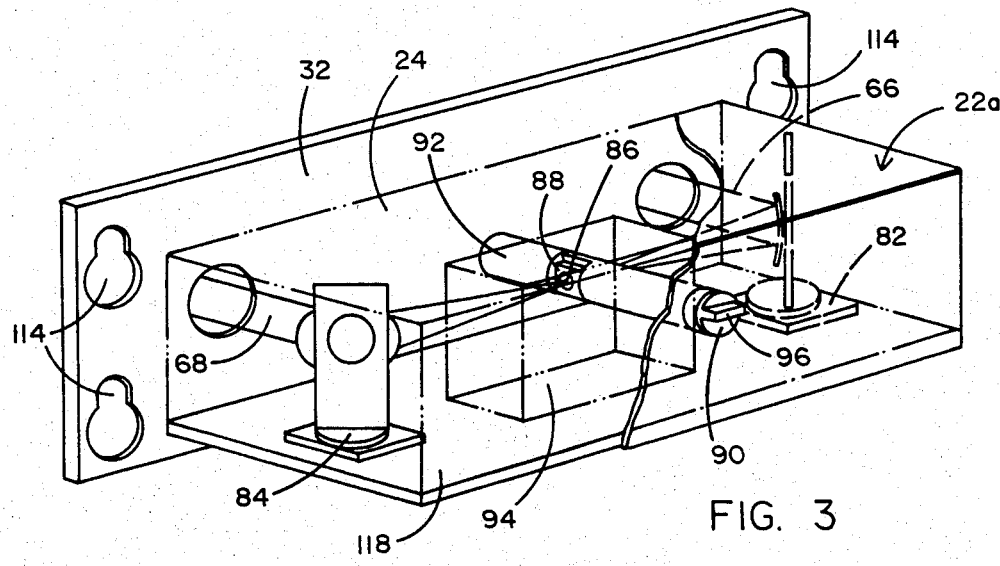
FIG. 3 is an isometric view showing a "zero" purge loss apparatus installed in a modular sampling chamber which provides transmittance illumination of the sample.

FIG. 3 shows schematically the incorporation of a minimal purge loss structure in one version of a sampling module 22a. The sampling chamber is fully enclosed by a housing, or shell, 24 having its rear wall, or panel, 32 secured to interface panel 30 of the spectrometer body 28 (FIG. 1). The sampling module interior includes mirror supports 82 and 84 which carry paraboloid reflectors having their common focal point at a sample 86. The sample, which may be solid or liquid, is mounted in a small metal block 88. The block is retained in position in a recess intermediate the ends of a plunger 90. This plunger, which is preferably cylindrical, has a close, sliding fit inside an elongated cylindrical tube 92, the fit being tight enough to substantially prevent air leakage into the sample chamber. Tube 92, in turn, extends through an aperture in the front wall of the sample chamber, and is secured in place in a supporting frame 94. The cylindrical body of the plunger 90 extends into tube 92 beyond the location of sample block 88. Thus one sample can be removed and another substituted without opening the chamber interior, because the inner end of the plunger still blocks the wall aperture during sample interchange. When the plunger holding the new sample is pushed back into the tube to locate the sample at the focal point of the beams, the only air brought into the chamber is that in the space around the small metal block 88. No delay is required for purging this amount of air. A knob 96 on the outer end of the plunger 90 facilitates manual control of the plunger's position.

Figure 4:
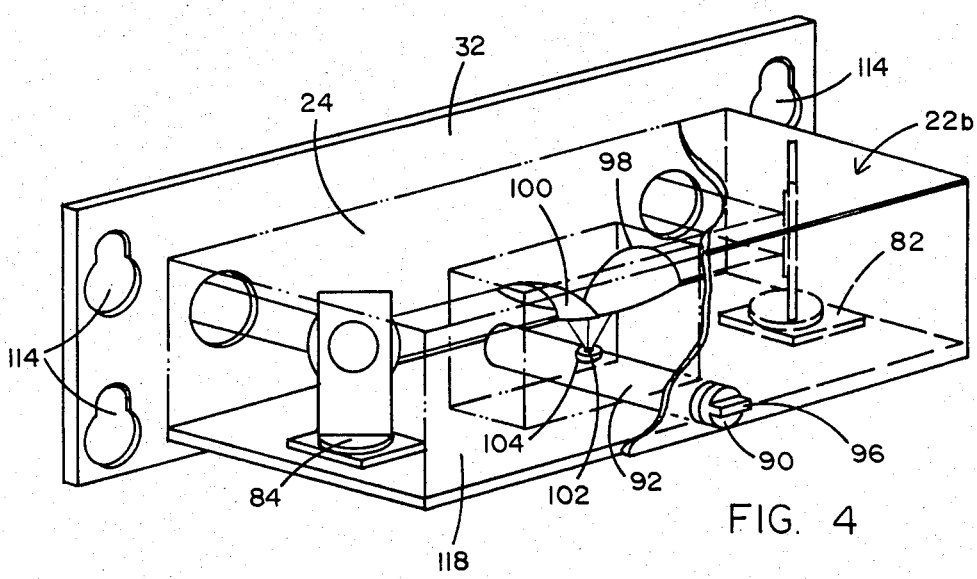
FIG. 4 is an isometric view showing a "zero" purge loss apparatus installed in a modular sampling chamber which provides reflectance illumination of the sample.

FIG. 4 shows the use of the purge retention structure in a sampling module 22b, which also incorporates optical elements used for reflectance analysis of a sample surface. Instead of two paraboloid reflectors, two flat mirrors are carried by mirror supports 82 and 84, thus providing collimated colinear beams in the chamber. Two paraboloid reflectors 98 and 100 have coinciding focal points at the surface of a sample 102, which may be a powder which causes diffuse reflectance, or a surface which causes specular reflectance. Assuming that the sample is a powder, its holder must face upwardly, as shown. As in the sampling module of FIG. 3, a plunger 90, having a knob 96, extends into a cylindrical tube 92. A small sample holder 104 is carried by plunger 90, and is brought into the sample-illuminating position by suitable adjustment of its position. As in the structure of FIG. 3, removal of one sample, and substitution of another, requires minimal air entry into the chamber, thus eliminating time loss for purging.

In the sampling modules of both FIGS. 3 and 4, the direct access to the sample chamber from its front surface is important in providing a relatively short distance through which the plunger 90 is required to extend. Vertical access would be possible in the module of FIG. 3, but not in the module of FIG. 4, where a powder sample must be held in place.

Figure 5:
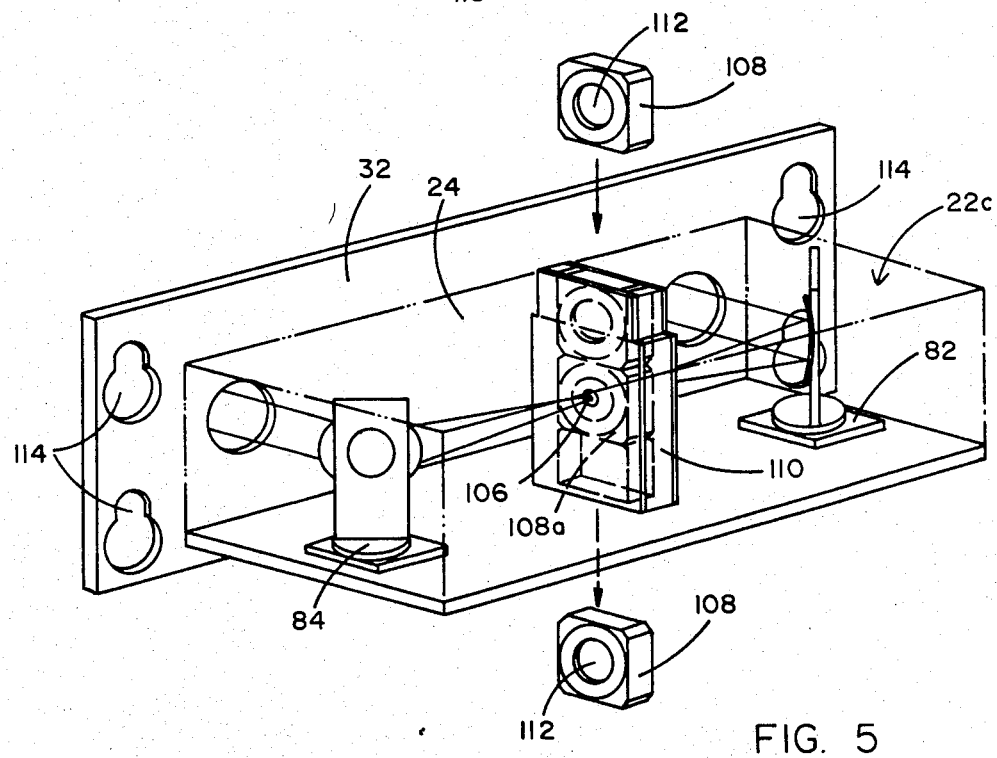
FIG. 5 is an isometric view of a "zero" purge loss apparatus installed in a modular sampling chamber in such a way as to permit continuous sample insertion through the top, and sample removal through the bottom, of the sampling chamber.

FIG. 5 shows a sampling module 22c designed to permit automated sample loading and unloading without purge loss. In this module, which is designed for transmittance of radiation through the samples, the adjustable mirror supports 82 and 84 carry paraboloid reflectors, whose common focal point is at the sample position 106. In order to permit particularly rapid insertion and removal of samples, which may be part of an automated process, the sample holders are inserted at the top of the chamber, moved to, and held at, the focal point during analysis, and then removed by "dropping out" at the bottom of the chamber. A plurality of sample holders 108 are shown in FIG. 5, each of which is a small metal block. Each metal block is shaped to fit in, and slide vertically downward through, a vertical channel-forming element, or chute, 110. Each sample holder has a centrally-located sample 112, through which the focused radiation passes when its holder is in the position shown at 108a. The samples may be solids or liquid cells. Because the metal blocks which act as sample holders are designed to fill the cross-sectional area in the vertical channel-forming element 110, the insertion and removal of samples is accomplished without purge loss.

As shown in each of the preceding figures, the wall 32 of sampling module 22 is adapted to be directly secured to the interface panel 30 of the spectrometer body (FIG. 1). Wall 32 is shown extending beyond the module housing 24. The extending portions have four "keyhole" apertures 114, the larger lower portions of which pass over the heads of thumb-screws 116 (see FIGS. 1 and 2) used to secure wall 32 tightly against interface panel 30 of the main body. The bodies of the screws fit closely in the smaller upper portions of the apertures 114; and the screw heads are tightened against wall 32.

Figure 6:
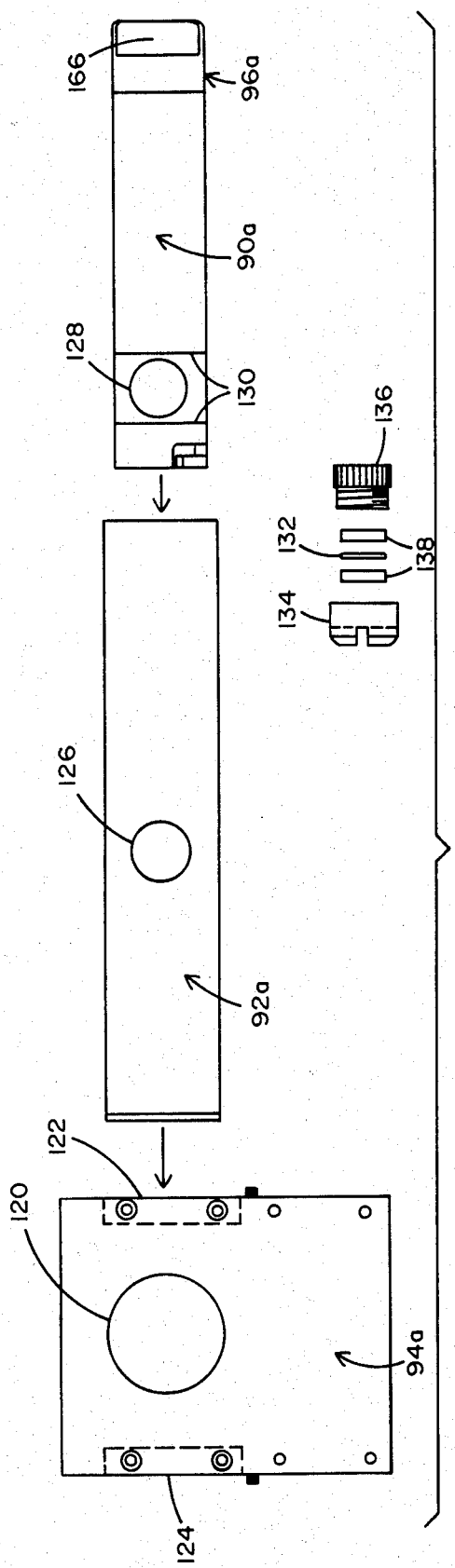

FIG. 6 shows the components of the purge-retaining apparatus of FIG. 3. The frame assembly 94a, which provides support for the other elements, is mounted in a fixed position on the floor 118 of the sampling chamber 22a (see FIG. 3). The frame 94a will normally be midway between the two mirror supports 82 and 84. Two aligned apertures 120 in the sides of frame 94 permit the analytical beam to pass through the sample. Two aligned apertures 122 and 124, in the front and rear surfaces, respectively, of frame 94a receive, and hold in place, the outer portion of the two part purge-conserving structure.

The outer portion of the purge-conserving structure is the hollow, tube-like member 92a, which, as shown in Figure 3, extends through both the apertures 122 and 124 in frame 94a. Suitable means, e.g., a dowel pin and a thumb-screw, may be used to hold the tube-like member 92a in position inside frame 94a. Two aligned apertures 126 in the wall of tube member 92a permit the analytical beam to pass through the sample, when apertures 126 are aligned with the apertures 120 in frame 94a.

The inner portion of the purge-conserving structure is the solid, plunger-like member 90a, which is inserted into, and has a closely-fitting relationship with, tube member 92a. The plunger-like member 90a is the sample-carrying member; and for that purpose has a transverse bore 128 extending through a recessed portion 130 of plunger member 90a. The sample, or specimen, holder is shown at 132. It is clamped between two annular members 134 and 136, the former being internally threaded and the latter externally threaded. Annular spacers 138 may be used to compensate for different thicknesses of the samples. After a sample holder is clamped between members 134 and 136, the sample-holding assembly is inserted into bore 128, with the center of the sample holder open for transmission of the radiation beam. When the bore 128 in plunger member 90a is pushed into alignment with the apertures 126 in tube member 92a, the sample is in position to be illuminated by the analytical beam.

Figure 8:
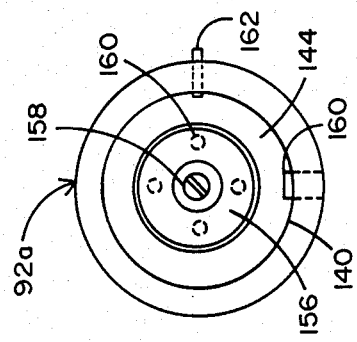
Figure 7:
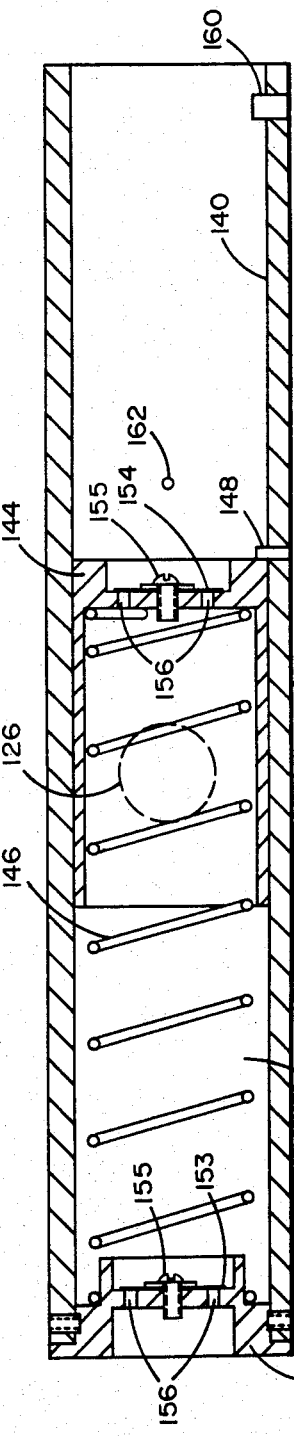

FIGS. 7-11, which show details and cross-sectional views of the tube member 92a and the plunger member 90a, may conveniently be considered together. As shown in FIGS. 7 and 8, the hollow, or tube, member 92a has an internal circumference 140 which fits the external circumference 142 (FIG. 10) of solid, or plunger, member 90a. Inside the left end of hollow tube member 92a is a piston 144, which is urged by a compression spring 146 toward the right, until it engages a stop 148 (e.g., a dowel pin). The left end of tube member 92a is closed by a plug 150, providing an isolated chamber 152 inside tube member 92a.

Chamber 152 has a special purging effect during removal and insertion of samples. It is provided with two one-way valves, e.g., rubber flapper valves 153 and 154, each of which is centrally held by a screw 155, and each of which covers a plurality of apertures 156 in its seated position. When plunger member 90a is fully inserted, and locked in position, with sample opening 128 aligned with sample opening 126, spring 146 is compressed, and chamber 152 has its minimum volume. During removal of plunger 90a for sample unloading, as a vacuum is created in chamber 152, the differential pressure on flapper valve 153 causes it to open, drawing into chamber 152 nitrogen gas from the interior of the sampling module. At the same time, the differential pressure on flapper valve 154 holds it closed, trapping the nitrogen gas in chamber 152.

After loading a new sample, the plunger 90a is pushed back into tube 92a, pushing piston 144 back toward the left. During this motion, the pressure increase in chamber 152 causes a differential pressure on flapper valve 153 which holds it in closed position, and also causes a differential pressure which opens flapper valve 154. The result is a forced flowing of nitrogen gas, through whatever escape passage exists, and over the surface of the sample, toward the right end of the structure. Thus, the sample-carrying assembly is automatically purged during insertion of a new sample. This is an additional purge-retention feature, over and above the atmosphere-blocking effect which exists because plunger 90a is not fully removed from tube 92a during sample interchange.

FIGS. 9-11 show details of the plunger member 90a which fits inside tubular member 92a. A longitudinal slot, or groove, 158 along the lower surface of plunger member 90a is in guiding engagement with a dowel pin 160 (FIG. 7) which extends through the wall of tubular member 92a into engagement with groove 158. This splined guiding connection keeps plunger member 90a properly oriented in the sampling chamber, i.e., prevents relative rotation of plunger member 90a and tubular member 92a, thereby keeping the sample at right angles to the focused radiation beam.

Additional alignment is provided by a dowel pin 162 (see FIGS. 7, 8 and 9), which serves several functions. As seen in FIG. 8, it extends through the wall of tubular member 92a, and extends beyond the wall both externally and internally. Its external projection engages a slot (not shown) in frame 94a for the dual purposes of preventing rotation of tubular member 92a after assembly, and of positioning tubular member 92a axially, by limiting its leftward movement when it is being inserted into frame 94a during assembly. (Rightward axial movement of the assembled tubular member 94a is prevented by a thumb screw, not shown). The internal dowel pin 162 also assists dowel pin 160 in preventing rotation of plunger member 90a. A longitudinally extending channel, or groove, in one side of plunger member 90a (which is not seen in the figures) creates a second splined guiding arrangement, the need for which will be explained below.

Several locking features are provided among the purge conserving components. Since plunger member 90a pushes against piston 144 and compressses spring 146 during sample insertion, it is necessary to lock it in the inserted position. This may be accomplished by engaging dowel pin 160 in a slot 164 provided in the periphery of knob member 96a. As shown in FIGS. 10 and 11, knob member 96a, which has a manual grip 166, is secured by a set screw 168 to a short shaft 170. Shaft 170 is mounted in a bearing (e.g., a Teflon ring) 172, which is fixed in the body of the plunger member by a set screw 174. Rotation of knob member 96a relative to plunger member 90a is limited to 90° by a dowel pin 176 which moves in an acurate groove 178, the groove being formed in one of the relatively movable members, and the dowel pin being secured to the other. This 90° relative rotation permits groove 164 to engage, and interlock with, dowel pin 160 when the sample is fully inserted. Note that FIG. 6 shows the unlocked position, in which grip 166 extends vertically, whereas FIGS. 10 and 11 show the locked position, in which grip 166 extends horizontally. Dowel pin 160 enters groove 164 through an access groove (not shown) which is aligned with the dowel pin in the unlocked position of knob 96a.

When the locking of dowel pin 160 in groove 164 has been accomplished, dowel pin 160 is no longer in engagement with longitudinal groove 158 to prevent rotation of the plunger member. At this time, that function is dependent on the engagement of dowel pin 162 in its longitudinal groove.

When plunger member 90a is first inserted into tubular member 92a, it is rotated through a 45° jog, which has the effect of preventing disengagement of the two members as the plunger member is being retracted to its sample loading and unloading position. In its fully inserted position, the plunger member engages piston 144 and holds spring 146 in compressed position; and the engagement of dowel pin 160 in slot 164 provides a lock. When this lock is disengaged, by turning knob member 96a, the spring force might eject the plunger member entirely, if a secondary locking arrangement were not provided. This secondary locking is effected by the engagement of dowel pin 160 with a wall 180 (see FIG. 10) near the left end of groove 158. A narrower groove 182 connects groove 158 to the left end of the plunger member. The narrower groove 182 is wide enough to receive dowel pin 148, but not wide enough to receive dowel pin 160. When dowel pin 160 engages wall 180, the left end of the plunger member remains inside the tubular member, and in engagement with piston 144.

If it is desired to remove plunger member 90a entirely from tubular member 92a, the former must be rotated 45° to bring dowel pin 160 into alignment with a groove 184 (see FIG. 9), which is wide enough to receive dowel pin 160, and which extends inward from the left end of plunger member 90a to intersect an arcuate groove 186 connecting to groove 158 on the right side (FIG. 10) of wall 180.

As previously explained, the sample holding subassembly 132-138 is inserted transversely into bore 128 in plunger member 90a. This sub-assembly is held in the proper transverse location by means of a small ball-plunger assembly 188 (see FIG. 9) which extends into a threaded opening 190 formed in the plunger member between its inner end and the sample recess 130.

A further feature of the plunger member and tubular member combination is the provision for passage of nitrogen through the plunger member as a new sample is being inserted. As previously stated, during retraction of the plunger member, nitrogen gas is sucked into chamber 152. After one sample has been removed from bore 128 in the plunger member, and another sample inserted in bore 128, the plunger member is pushed back into the tubular member. (During sample interchange, bore 128 was accessible to the operator, but the left end of the plunger member continued to block the right end of the tubular member, thus blocking the entrance of atmosphere).

As plunger member 90a is pushed back into sample-illuminating position, it engages piston 144, moving the piston toward the left. Reduction of the volume of chamber 152 forces nitrogen past valve 154, through an air channel 192 (FIG. 9) into the sample-containing recess 130. Nitrogen also passes through groove 158 to recess 130. Nitrogen is thus forced to "wash" over both surfaces of the sample, as it moves to escape toward the right end of the plunger member. After purging any atmosphere in the sample recess, the nitrogen passes through groove 158 toward the right end of the plunger member. It also moves through the longitudinal groove on the far side of the plunger member, which groove extends from the left end of the plunger member to an annular groove 194 which provides communication between the two longitudinal grooves. None of the dowel pins 148, 160 or 162 blocks nitrogen flow along the grooves. Although dowel pin 160 and 162 fit their respective grooves laterally, in order to serve as guides, they do not project radially far enough to reach the inner surfaces of the grooves.

FIG. 12 shows the components of the purge-retaining apparatus of FIG. 4. Whereas FIGS. 3 and 6 show a zero purge transmittance module, FIGS. 4 and 12 show a zero purge reflectance module. The frame assembly 94b of FIG. 12, which provides support for the other elements, is mounted in a fixed position on the floor 118 of the sampling module 22b (see FIG. 4). The frame 94b will normally be midway between the two mirror supports 82 and 84. Two aligned apertures 122b and 124b, in the front and rear surfaces, respectively, of frame 94b receive, and hold in place, the outer portion of the two part purge-conserving structure, which comprises the tubular member 92b and the plunger member 90b.

Figure 15:
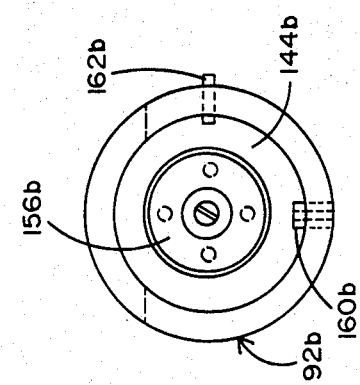
Figure 13:
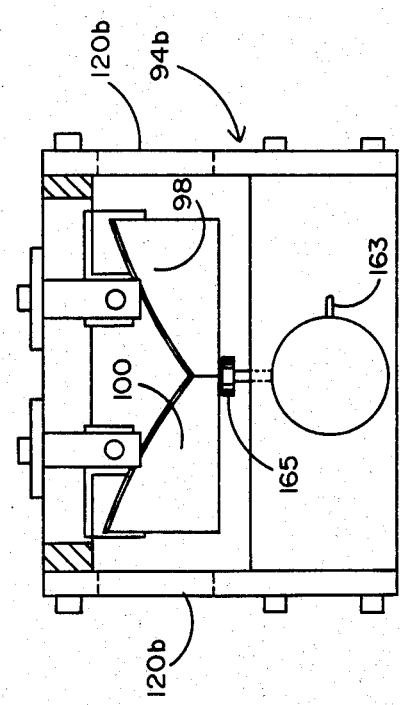
Figure 14:
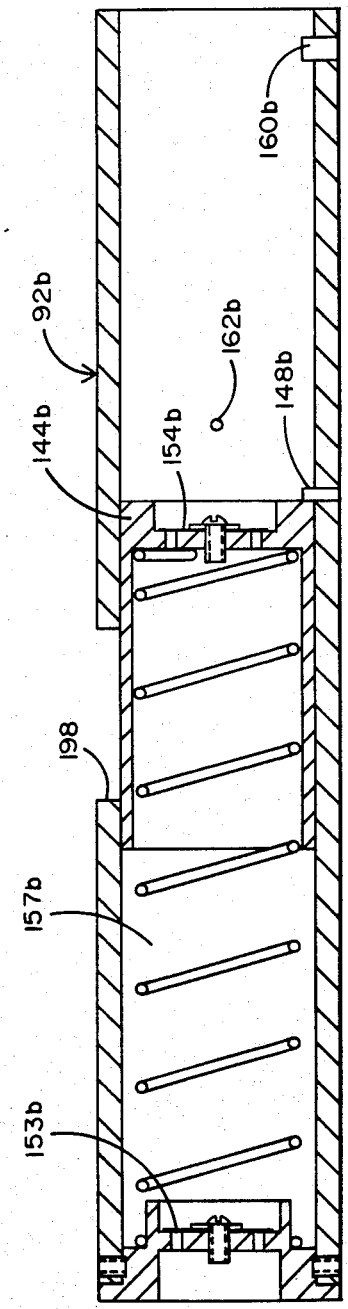

FIG. 13 shows a front elevation of frame member 94b. Because this is a reflectance module, the radiation beams on both sides of frame member 94b are collimated beams, which pass through aligned apertures 120b in the sides of the frame member. These beams are reflected by the two paraboloid reflectors 98 and 100, which have coinciding focal points at the surface of a sample, which is carried by plunger member 90b, and is located below the paraboloid reflectors. FIG. 13 shows a slot 163, which receives dowel pin 162b projecting from tubular member 92b (see FIG. 15). When the dowel pin hits the far end of the slot, further inward movement of tubular member 92b into frame 94b is blocked. A set screw 165 mounted in frame 94b engages the outer surface of tubular member 92b to prevent outward movement of the latter from its assembled position. Similar dowel/slot and set screw features (not shown) are provided in the structure of FIGS. 6–11.

As shown in FIG. 12, a sample holder 196 is adapted to carry a reflecting sample (diffuse or specular), and is supported by, and at the top of, plunger member 90b. Because of the possible use of a powder sample, the horizontal position of sample holder 196 must be maintained at all times. When plunger member 90b is fully inserted in tubular member 92b, the sample will be viewed through an aperture 198 in the top of the tubular member. Arrangements are included to raise and lower the sample holder. It is in its lowered position during insertion and retraction of the plunger; and when fully inserted it is raised into the desired position for illumination. The vertical direction in FIG. 12 of grip 166b on knob 96b corresponds to the lowered position, inside plunger member 90b, of the platform on which sample holder 196 is supported.

There are several similarities between the relationship of plunger and tubular members 90b and 92b of the reflectance module and the relationship of plunger and tubular members 90a and 92a of the transmittance module (FIG. 6). For example, they have the same close fitting diameters in order to block ingress of atmosphere. They have the same 45° jog in a channel, or groove, 158b at the inner end of the plunger member 90b, which serves to prevent accidental ejection of plunger member 90b from the right end of tubular member 92b.

Details of plunger and tubular members 90b and 92b are shown in FIGS. 14-18. The longitudinal groove, or channel, 158b in the plunger member is guided by dowel pin 160b in the tubular member. Also, another dowel pin 162b guides a second longitudinal channel in the wall of the tubular member (not shown) in the plunger member. The two longitudinal channels are interconnected by an annular channel, or groove, 194b. The tubular member 92b (FIG. 14) has the same internal spring-loaded piston 144b, and one-way flapper valves 153b and 154b, as the transmittance module. So chamber 152b provides the same function of drawing in nitrogen when the chamber is expanding, and expelling it past the sample when the chamber is contracting. The rightward movement of piston 144b is limited by a dowel pin 148b.

As shown in FIGS. 16-18, the sample holder 196 is raised and lowered by a cam, which is controlled by the 90° rotation of the knob 96b. In this version, rotation of knob 96b causes rotation of a long shaft 200, which is caused by a set screw 202 to rotate with the knob, and which rotates in a bearing 204. Near the left end of shaft 200, it is held in engagement with a cam 208 by a set screw 206. The upper position of cam 208 is shown in FIGS. 17 and 18, and its lower position is shown in FIG. 16. Support for sample holder 96 is provided by an elevator 210, which is raised and lowered by cam 208. Elevator 210 is limited to vertical movement by its engagement with the sides of a vertical bore 212 provided in plunger member 90b. A dowel pin 214 (FIG. 16), carried by elevator 210, causes clockwise motion of the cam 208 (as seen in FIG. 16) to move elevator 210 downwardly. Counter-clockwise rotation of cam 15 208 causes it to push against a horizontal surface 216 of the elevator 210 to move the latter upwardly. Movement of elevator 210 with respect to shaft 200 is accommodated by an elongated slot 218 in the lower extension 220 of the elevator.

Rotation of knob member 96b thus has a dual function in this version. The same 90° relative rotation between knob member 96b and plunger member 90b is permitted by a dowel pin 176b moving in an acurate slot 178b. In addition to bringing peripheral groove 164b in knob member 96b into locking engagement with dowel pin 160b (in the tubular member), this rotation causes cam 208 to raise elevator 210 to its upper position, thereby placing the sample in the proper position for illumination.

The forced purging of the sample area during insertion of plunger member 90b, after a sample interchange, is essentially the same in the reflectance module as in the transmittance module, previously described in detail.

Figure 20:
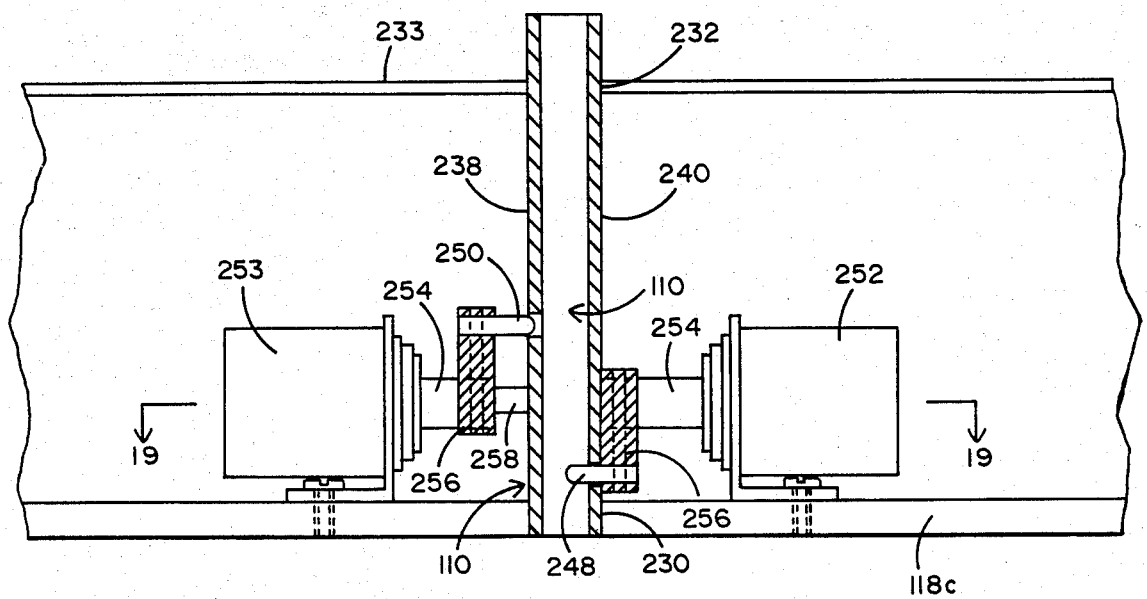
Figure 21:
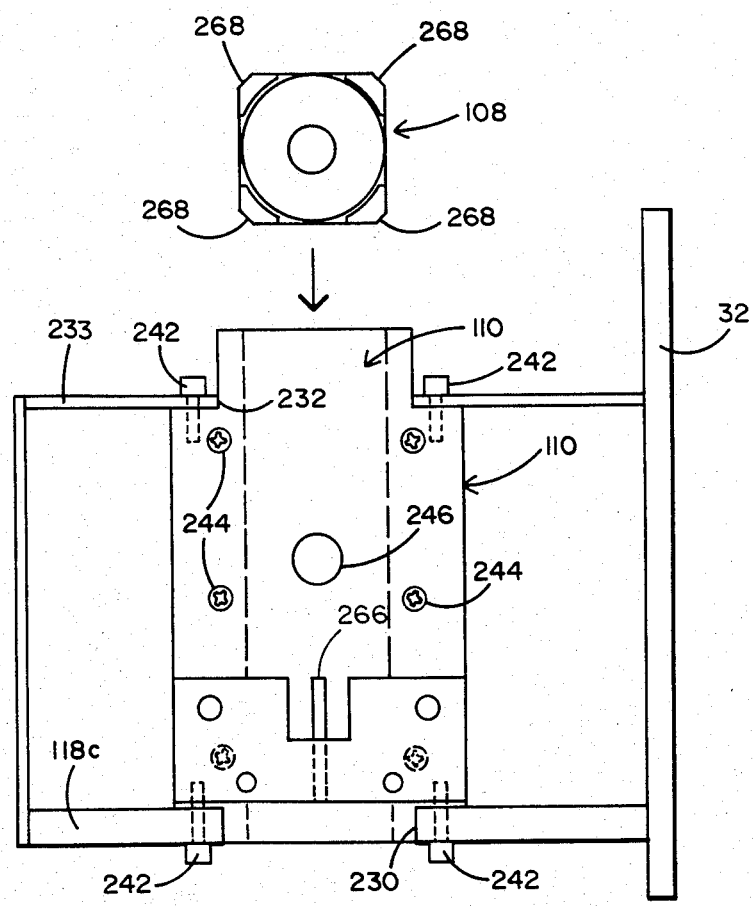

The remaining embodiment of the purge-conserving modules illustrated in the present application is the one briefly described in the discussion of FIG. 5. Details of this embodiment are shown in FIGS. 19-21. This is a very staight-forward mechanical arrangement, made possible by the ready accessibility of the upper and lower walls of the sampling enclosure. As seen in FIGS. 20 and 21, the channel-forming element, or chute, 110, through which the sample holders 108 pass, extends into a rectangular aperture 230 in the floor 118c of the modular sample chamber 22c, and extends through and beyond a rectangular aperture 232 in the top wall 233 of the modular sample chamber.

The cross-sectioned portion of FIG. 19, which is taken on the line 19—19 of FIG. 20, shows the vertical walls of chute 110. They may be formed to two relatively thick side spacers 234 and 236, and two relatively flat side plates 238 and 240. The two side spacers 234 and 236 are shown secured to the floor and top of the modular chamber by a plurality of cap screws 242 (FIG. 21); and the side plates 238 and 240 are shown secured to side spacers 234 and 236 by a plurality of flat head screws 244 (FIG. 21).

As the sample holders 108, carrying sample 112, pass vertically downward through the chute 110, they are temporarily positioned by electrically operated shuttle devices. Two shuttle devices are shown: a device at the right side of the chute (FIG. 20) adapted to provide support for the lowest sample holder in the chute, and a device at the left of the chute adapted to provide support for the sample holder whose sample is positioned for illumination by the focused analytical beam. The beam passes through apertures 246 (FIG. 21) in the side plates 238 and 240 of the chute. It is desirable that the lower sample holder be held in the chute during illumination of the one above it, and that a top sample holder be resting on the one being illuminated, in order to minimize access of atmosphere to the purged interior of the spectrometer system. Even is "dummy" sample holders (not containing samples) are used, this filling of chute 110 should be maintained. Since each sample is recessed in its sample holder, there is a small space for the internal purge to "bleed out", and thus continuously purge the sample area.

In the cross-sectioned portion of FIG. 20, which is taken on the line 20—20 of FIG. 19, the lower shuttle support has two pins 248 extending into the chute to support the sample holders, and the upper shuttle support has two pins 250 in retracted position. Each shuttle operating device comprises a solenoid 252 and 253, a solenoid shaft 254, and a shuttle plate 256 which carriers the pins (248 or 250). The solenoids are suitably secured to the floor of the sample chamber as shown in FIG. 20.

Two shuttle-supporting shafts 258 (FIG. 19) extend, respectively, through two linear bearings 260 which are located in bores provided in the respective side spacers 234 and 236, and which are retained in position by set screws 262. The two shuttle plates 256 are constrained to move simultaneously because set screws 264 secure each shuttle plate to each supporting shaft 258. Each solenoid shaft 254 is secured to its respective shuttle plate 256 by a dowel pin 266.

As stated above, the chute 110 should normally be loaded with three sample holders. During analytical illumination, the stack of three sample holders is supported by the lower pins 248, which are in the extended position as shown in FIGS. 19 and 20. The middle sample is the one being illuminated. After it has been analyzed, an electrical control system (preferably computer operated) energizes solenoid 252, which pulls both shuttle plates 256, and their respective pins 248 and 250, toward the right. The relative pin locations are such that pins 250 extend into the chute before pins 248 are fully retracted from the chute. Thus, there is a brief period during which both the bottom and middle sample holders are individually supported by the pins. Because the pins are just inside the corners of the chute (see FIG. 19), they fit into the notched corners 268 of the sample holders 108 (see FIG. 21). Therefore, when pins 250 enter the chute, they are not blocked by either sample holder.

When pins 248 reach their fully retracted position, the bottom sample holder drops out. At this time, the middle and upper sample holders are being supported by pins 250. Promptly, solenoid 253 is energized, thereby retracting pins 250 from the chute, and causing pins 248 to re-enter the chute. As soon as pins 250 have been fully retracted from the chute, the sample holders will automatically drop to rest on pins 248. This brings the upper sample holder into the middle, or illumination, position; and a new sample holder is inserted at the top of the chute.

Arrangements may be made for automatic transfer of sample holders into the top of the chute, and for automatic transfer of sample holders from the bottom of the chute.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. In a spectrometer having a wall-enclosed body space, a readily accessible wall-enclosed sample space wherein sample illumination occurs, and means for maintaining a non-atmospheric gas purge in both of the enclosed spaces, purge retention apparatus which avoids substantial purge loss during sample insertion into, and removal from, the sample space comprising:
a hollow guiding member which extends from the exterior into the interior of the sample space beyond the sample-illuminating position and which is secured in position; and
a sample-carrying member which is insertable into the interior of the hollow guiding member to advance the sample toward the sample-illuminating position, and which has a close exterior fit into the guiding member, and a generally closed interior construction, in order to substantially block flow of atmosphere into the gas purged interior of the sample and spectrometer spaces.

2. The apparatus of claim 1 wherein:
the hollow guiding member is a tube having an opening therethrough at the sample-illuminating position; and
the sample-carrying member is a plunger which carries the sample in a recess intermediate its inner and outer ends, and which is retracted, but not removed, from the tube for sample unloading and reloading.

3. The apparatus of claim 2 which also comprises:
means for locking the plunger in its inserted position in the tube.

4. The apparatus of claim 3 wherein the locking means comprises:
a manually rotatable member mounted on the outer end of the plunger, having an arcuate groove therein extending at right angles to the axis of the plunger; and
a member carried by the tube which is brought into locking engagement with the groove by rotation of the rotatable member.

5. The apparatus of claim 4 which also comprises:
camming means operated by rotation of the manually rotatable member to raise and lower the sample.

6. The apparatus of claim 2 which also comprises:
means for preventing removal of the plunger from the tube until the plunger has been rotated with respect to the tube.

7. The apparatus of claim 1 which also comprises:
purging means for automatically forcing non-atmospheric gas purge past the sample toward the exterior of the sample space as the sample-carrying member is being inserted into the interior of the hollow guiding member.

8. The apparatus of claim 7 wherein the purging means comprises:
a chamber in the hollow guiding member which contracts as the sample-carrying member is inserted, and expands as the sample-carrying member is retracted;
a one-way valve between the chamber and the interior of the sample space, which is closed during contraction of the chamber and is open during expansion of the chamber; and
a one-way valve between the chamber and the exterior of the sample space, which is open during contraction of the chamber and is closed during expansion of the chamber.

9. The apparatus of claim 7 which also comprises:
air passages which direct the flow of the gas purge past the sample.

10. The apparatus of claim 1 wherein:
the hollow guiding member extends through the sample space and is accessible through opposite walls of the enclosed sample space; and
the sample-carrying member enters the hollow guiding member through one wall of the sample space and exits the hollow guiding member through the opposite wall of the sample space.

11. The apparatus of claim 10 wherein the sample-carrying member enters through the top of the sample space and exits through the bottom of the sample space.

12. The apparatus of claim 10 wherein the cross-sectional shapes of the interior of the hollow guiding member and of the exterior of the sample-carrying member are rectangular.

13. The apparatus of claim 11 wherein the cross-sectional shapes of the interior of the hollow guiding member and of the exterior of the sample-carrying member are rectangular.

14. The apparatus of claim 13 which also comprises:

temporary supporting means for the sample-carrying member movable back and forth at right angles to the guiding member, in order to be projected into, or retracted from, the interior of the guiding member.

15. The apparatus of claim 14 which also comprises: power-operated means for controlling the back and forth movement of the supporting means.

16. The apparatus of claim 14 wherein:
the chute is adapted to contain three or more vertically stacked sample-carrying members; and
the supporting means comprises vertically spaced supporting pins which are adapted to engage the lower edges of the bottom and middle sample-carrying members, respectively.

17. In a spectrometer having a wall-enclosed body space, a readily accessible wall-enclosed sample space wherein sample illumination occurs, and means for maintaining a non-atmospheric gas purge in both of the enclosed spaces, a method for maintaining the purged condition during sample loading and unloading, comprising:
locating in the sample space a hollow non-moving guiding member which provides a sample-illuminating position for a sample;
inserting into the guiding member a movable sample-carrying member which fits inside the guiding member and which substantially blocks atmosphere from the purged spaces and from the interior of the sample-carrying member;
moving the sample-carrying member from a sample-illuminating position to a sample loading/unloading position without allowing atmosphere to enter the purged spaces;
loading a sample in the sample-carrying member while the atmosphere remains blocked from the purged spaces; and
moving the sample-carrying member back into the sample illuminating position without injecting a substantial amount of atmosphere into the purged spaces.

18. The method of claim 17 which also comprises:
turning a rotatable member associated with the sample-carrying member in order to simultaneously (a) move the sample and (b) lock the sample-carrying member in its sample illuminating position.

19. The method of claim 17 which also comprises:
forcing non-atmospheric gas purge past the sample toward the exterior of the sample space as the sample-carrying member is being moved toward its sample illuminating position.

20. In a spectrometer having a wall-enclosed body space, a readily accessible wall-enclosed sample space wherein sample illumination occurs, and means for maintaining a non-atmospheric gas purge in both of the enclosed spaces, a method for maintaining the purged condition during sample loading and unloading, comprising:
locating in the sample space a hollow non-moving guiding member which provides a sample-illuminating position for a sample;
inserting into the guiding member a movable sample-carrying member which fits inside the guiding member and which substantially blocks atmosphere from the purged spaces and from the interior of the sample-carrying member;
causing the sample-carrying member to move downwardly into its sample-illuminating position;
supporting the sample-carrying member in its position during sample illumination;
inserting another sample-carrying member into the guiding member above the supported sample-carrying member;
permitting each sample-carrying member to move downwardly after its illumination; and
removing each sample-carrying member from the guiding member below its sample-illuminating position.

* * * * *